United States Patent [19]

Miller

[11] Patent Number: 5,846,716
[45] Date of Patent: Dec. 8, 1998

[54] METHOD FOR NUCLEOTIDE SEQUENCE AMPLIFICATION

[75] Inventor: Glen A. Miller, Hopkinton, Mass.

[73] Assignee: Genzyme Corporation, Framingham, Mass.

[21] Appl. No.: 592,145

[22] Filed: Jan. 26, 1996

Related U.S. Application Data

[62] Division of Ser. No. 326,432, Oct. 18, 1994, Pat. No. 5,545,539.

[51] Int. Cl.$^6$ ............................. C12Q 1/68; C12P 19/34; C12N 15/00; C07H 21/00
[52] U.S. Cl. ............................. 435/6; 435/91.2; 435/975; 935/77; 536/25.4
[58] Field of Search ............................. 435/6, 91.2, 975; 935/77; 536/25.4

[56] References Cited

U.S. PATENT DOCUMENTS

| | | | |
|---|---|---|---|
| 4,795,699 | 1/1989 | Tabor et al. | 435/5 |
| 4,997,932 | 3/1991 | Reardon et al. | 536/27 |
| 5,192,659 | 3/1993 | Simons | 435/6 |
| 5,386,024 | 1/1995 | Kacian et al. | 536/25.4 |
| 5,545,540 | 8/1996 | Mian | 435/91.2 |

OTHER PUBLICATIONS

S. Andrew et al., "The Relationship Between Trinucleotide (CAG) Repeat Length and Clinical Features of Huntington's Disease", *Nature Genetics*, 4:398–403, (1993).
J. Annemieke et al., "Identication of a Gene (FMR–1) Containing a CGG Repeat Coincident With a Breakpoint Cluster Region Exhibiting Length Variation in Fragile X Syndrome", *Cell*, 65:905–914, (1991).
C. Aslanidis et al., "Cloning of the Essential Myotonic Dystrophy Region and Mapping of the Putative Defect", *Nature*, 355:548–551, (1992).
L. Barron et al., "A Single Allele From the Polymorphic CCG Rich Sequence Immediately 3' to the Unstable CAG Trinucleotide in the IT15 cDNA Shows Almost Complete Disequilibrium With Huntington's Disease Chromosomes in the Scottish Population", *Human Molecular Genetics*, 3:173–175, (1994).
J. Buxton et al., "Detection of an Unstable Fragment of DNA Specific to Individuals With Myotinic Dystrophy", *Nature*, 355:347–348 (1992).
Y.–H. Fu et al., "An Unstable Triplet Repeat In a Gene Related to Myotonic Muscular Dystrophy", *Science*, 255:1256–1258, (1992).
Y. Goldberg et al., "A PCR Method for Accurate Assessment of Trinucleotide Repeat Expansion in Huntington Disease", *Human Molecular Genetics*, 2:635–636 (1993).
J. Ian et al., "Over–representation of the Disease Associated (CAG) and (CGG) Repeats in the Human Genome", *Nucleic Acids*, 22:1735–1740, (1994).
H. Harley et al., Expansion of an Unstable DNA Region and Phenotypic Variation in Myotinic Dystrophy, *Nature*, 355: 545–546 (1992).
X. Hauge et al., "Study of the Origin of 'Shadow Bands' Seen When Typing Dinucleotide Repeat Polymorphisms by the PCR", *Human Molecular Genetics*, 2:411–415, (1993).

R. Koide et al., "Unstable Expansion of CAG Repeat in Hereditary Dentatorubral–Pallidoluysian Atrophy (DRPLA)", *Nature Genetics*, 6:9–13, (1994).
S. Knight et al., "Trinucleotide Repeat Amplification and Hypermethylation of a CpG Island in FRAXE Mental Retardation", *Cell*, 74:127–134, (1993).
E. Kremer et al., "Mapping of DNA Instability at the Fragile X to a Trinucleotide Repeat Sequence p(CCG)n", *Science*, 252:1711–1714, (1991).
A. La Spada et al., "Androgen Receptor Gene Mutations in X–linked Spinal and Bulbar Muscular Atropy", *Nature*, 352:77–79, (1991).
M. Litt et al., "Shadow Bands Seen When Typing Polymorphic Dinucleotide Repeats: Some Causes and Cures", *BioTechniques*, 15:280–284, (1993).
The Huntington Disease Collaborative Research Group, "A Novel Gene Containing a Trinucleotide Repreat That Is Expanded and Unstable on Huntington's Disease Chromosomes", *Cell*, 72:971–983, (1993).
W. Melchior, Jr. et al., "Alteration of the Relative Stability of dA dT and dG dC Base Pairs in DNA", *Proc. Nat. Acad. Sci.*, 70:298–302, (1973).
S. Miller et al., "A Simple Salting Out Procedure for Extracting DNA from Human Nucleated Cells", *Nucleic Acids Research*, 16:1215, (1988).
H. Orr et al., "Expansion of an Unstable Trinucleotide CAG Repeat in Spinocerebellar Ataxia Type 1", *Nature Genetics*, 4:221–226, (1993).
W. Rees et al., "Betaine Can Eliminate the Base Pair Composition Dependence of DNA Melting", *Biochemistry*, 32:137–144, (1993).
O. Riess et al., "Improved PCR Conditions for the Stretch of $(CAG)_n$ Repeats Causing Huntington's Disease", *Human Molecular Genetics*, 2:637, (1993).
R. Snell et al., "Relationship Between Trinucleotide Repeat Expansion and Phenotypic Variation in Huntington's Disease", *Nature Genetics*, 4:393–397, (1993).
R. L. Stallings, "Distribution of Trinucleotide Microsatellites in Different Catgories of Mammalian Genomic Sequence: Implications for Human Genetic Disease", *Genomics*, 21:116–121 (1994).
J. Valdes et al., "A Simple Non–radioactive Method for Diagnosis of Huntington's Disease", *Human Molecular Genetics*, 2:633–634, (1993).
P. von Hippel et al., "DNA–Protein Interactions", *Annual Review Biochemistry*, 41:231–300, (1972).
S. Yu et al., "Fragile X Genotype Characterized by an Unstable Region of DNA", *Science*, 252:1179–1181, (1991).

Primary Examiner—Francisco Prats

[57] ABSTRACT

This invention relates to an improvement of the procedure for amplifying a target nucleotide sequence by using an effective amount of a glycine-based osmolyte in the reaction mixture of an amplification procedure. It has been found that the use of a glycine-based osmolyte reduces the appearance of stutter bands in the amplification product allowing for easier detection of the target nucleotide sequence. For example, detection of the target trinucleotide repeat sequence, indicative of Huntington's Disease, is made clearer with the use of a glycine-based osmolyte.

3 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( v ) FRAGMENT TYPE: N-terminal ( x i ) SEQUENCE DESCRIPTION: SEQ ID NO:1:

GCGGCTGAGG AAGCTGA                                    17

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCGGCTGAGG AAGCTGA                                    17

METHOD FOR NUCLEOTIDE SEQUENCE AMPLIFICATION

This application is a divisional of U.S. Ser. No. 08/326,432 filed Oct. 18, 1994 now U.S. Pat. No. 5,545,539.

BACKGROUND OF THE INVENTION

Surveys of human genomic DNA have indicated that tandemly reiterated sequences are present in abundance (Stallings, *Genomics*, 1994. 21: p. 116–21; Han et al., *Nucleic Acids Res.*,1994. 22(9): p. 1735–40). The polymorphic nature of these sequences has fostered their use in a variety of studies. Recently a number of human diseases have been shown to be caused by the expansion of a subset of these repetitive sequences, trinucleotide repeats (HDCRG, Cell, 1993, 72(6): p. 971–83; Fu et al., *Science*, 1992. 255(5049): p. 1256–8; Knight et al., *Cell*, 1993, 74(1): p. 127–34; Orr et al., *Nat Genet*, 1993, 4(3): p. 221–6; Harley et al., *Nature*, 1992, 355(6360): p. 545–6; Buxton et al., *Nature*, 1992, 355(6360): p. 547–8; Aslanidis et al., *Nature*, 1992, 355(6360): p. 548–51; La-Spada et al., *Nature*, 1991. 352(6330): p. 77–9; Sutherland et al., *Lancet*, 1991, 338(8762): p. 289–92; Yu et al., *Science*, 1991, 252(5010): p. 1179–81; Kremer et al., *Science*, 1991. 252 (5013): p. 1711–4; Verkerk et al., *Cell*, 1991, 65(5): p. 905–14; Koide et al., *Nat Genet*, 1994, 6(1): p. 9–13).

All of the currently known diseases caused by trinucleotide repeats are caused by repeats high in dG+dC (guanine and cytosine respectively) content (Han et al., 1994). One method for analyzing the expansion of such repeats is by amplifying the region using the polymerase chain reaction (PCR). The high dG+dC content renders amplification and/or DNA sequencing very difficult due to an increased melting temperature, or $T_m$, and stable secondary structure of the expanded motif. A common result of amplifying a region containing a repeat motif with a high dG+dC content is the presence of additional amplification products which do not correspond to the desired product (Hauge et al., *Hum. Molec. Genet.*, 1993, 2(4): p. 411–15). Such "stutter" or "shadow" banding complicates the interpretation of results of an assay. A number of authors have noted the difficulty in interpreting the banding patterns seen in Huntington's disease (HD) (Riess, O., et al., *Hum Mol Genet*, 1993, 2(6): p. 637; Goldberg et al., *Hum Mol Genet*, 1993. 2(6): p. 635–6; Valdes et al., *Hum Mol Genet*, 1993, 2(6): p. 633–4; Snell et al., *Nat Genet*, 1993, 4(4): p. 393–7; Barron et al., *Hum. Molec. Genet.*, 1994, 3(1): p. 173–175).

Several theories addressing the problem of "stutter" or "shadow" banding have been put forth (Litt et al., *Biotech.*, 1993, 15(2): p. 280–284). Possible mechanisms resulting in false banding patterns may include improper primer annealing to a repetitive sequence or strand slippage during synthesis. A third explanation proposes that secondary structure unique to the repetitive sequences allow the extending DNA strand to skip cassettes of repeats. If this were to occur during the early cycles of a PCR reaction sufficient template could be made which would eventually appear as additional or "stutter" bands. Secondary structure resulting in additional banding may be caused by the increased stability of a region with an increased dG+dC content. The differential stability of base pairs has been a subject of inquiry for over three decades. Phosphate binding cations have long been known to be general destabilizers of the DNA helix (von Hippel et al.,*Ann. Rev. Biochem.*, 1972, 41: p. 231–300) The most likely mechanism for this alteration of helical stability is the affect that these cations ($Cs^+$, $Li^+$, $Na^+$, $K^+$, $Rb^+$, $Mg^{++}$, $Ca^{++}$) have on the transfer of free energy of a nucleotide from a non-aqueous to an aqueous environment (von Hippel et al., 1972). These cations effectively increase the solubility of nucleotides in aqueous solutions which acts to destabilize the helix in a general fashion.

Another class of compounds has been shown to alter relative stability of the DNA helix based on nucleotide composition. Various tetraalkylammonium ions are known to preferentially bind in DNA grooves at dA•dT base pairs (Melchior et al., *PNAS*, 1973, 70(2): p. 298–302). The mechanism in this case relies on the differential levels of hydration between base pairs and the size of the tetraalkylammonium ion being used. Previous work has suggested that dA•dT base pairs are more highly hydrated than dG•dC base pairs thus providing a relatively more suitable binding site for the nonpolar arms of alkylammonium ions (Tunis et al., *Biopolymers*, 1968, 6: p. 1218–1223). It has also been demonstrated that larger tetraalkylammonium ions are general destabilizers of DNA while smaller tetraalkylammonium ions have a differential stabilization effect based on base composition (Melchior et al., 1973). The overall effect, in this case, is to produce a relative isostabilization of the dA•dT base pairs relative to dG•dC base pairs thus eliminating the base composition contribution to the $T_m$ of a DNA sequence. Isostabilization is desirable in determining a $T_m$ at which DNA secondary structure would be minimal. The use, however, of tetraalkylammonium compounds in these studies is offset by their destabilization effect on DNA-protein interactions at the salt concentrations necessary to achieve DNA isostabilization (Rees et al.,*Biochemistry*, 1993, 32(1): p. 137–44).

There is a need for a compound which would offer the isostabilizing effect of the tetraalkylammonium compounds without the DNA-protein altering side effects.

SUMMARY OF THE INVENTION

This invention relates to an improvement of the procedure for amplifying a target nucleotide sequence, by using an effective amount of a glycine-based osmolyte in the reaction mixture of the amplification procedure. It has been found that the use of a glycine-based osmolyte reduces the appearance of stutter bands in the amplification product allowing for easier detection of the target nucleotide sequence. For example, detection of the target trinucleotide repeat sequence, indicative of Huntington's Disease, is made clearer with the use of a glycine-based osmolyte.

The present invention further relates to a kit for amplifying a target nucleotide sequence for diagnostic analysis, wherein the kit includes a glycine-based osmolyte to be used in the amplification procedure.

This invention, in addition, relates to the improvement of sequencing a target nucleotide sequence, the improvement comprising adding an effective amount of a glycine-based osmolyte to the reaction mixture of an sequencing procedure.

DETAILED DESCRIPTION OF THE INVENTION

This invention is based upon the discovery that when a glycine-based osmolyte is added to a PCR amplification reaction mixture for the detection of Huntington's disease the resultant product of the amplification procedure is more interpretable. The glycine-based osmolyte offers the isostabilizing effect of the tetraalkylammonium compounds without its DNA-protein altering side effects.

The term "amplifying" refers to the repeated copying of sequences of deoxyribonucleic acids (DNA) or ribonucleic acids (RNA) through the use of specific or non-specific means resulting in an increase in the amount of the specific DNA or RNA sequences intended to be copied. These processes include the Polymerase Chain Reaction (PCR), Nucleic Acid Sequence Based Amplification (NASBA), Transcription-based Amplification System (TAS), Self-sustained Sequence Replication (3SR), 0-beta replicase, Ligation amplification reaction (LAR) and Ligase Chain Reaction (LCR).

A glycine-based osmolyte suitable for use in the present invention includes trimethylglycine, glycine, sarcosine and dimethylglycine.

The term "target nucleotide sequence" refers to a portion of a nucleotide sequence, the presence of which is indicative of a condition, such as a disease. Such "target nucleotide sequences" would include, but not be limited to, nucleotide sequence motifs or patterns specific to a particular disease and causative thereof, nucleotide sequences specific as a marker of a disease, and nucleotide sequences of interest for research purposes which may not have a direct connection to a disease. In general, "target nucleotide sequences" could be any region of contiguous nucleic acids which are amenable to an amplification technology.

The term "sequencing" refers to the copying of a target nucleotide sequence via biochemical processes. Such "sequencing" refers to the determination of the deoxyribonucleic or ribonucleic acid composition of a target nucleotide sequence and the order in which those nucleic acids occur in that sequence. A typical enzymatic sequencing procedure would entail the isolation of a region of contiguous double stranded nucleic acids, separating them into their component single strands, adding a sequencing primer homologous to a portion of the aforementioned region and through the use of nucleic acid polymerase enzymes synthesizing a complementary stretch of nucleic acids. In one scheme known as Sanger or dideoxy sequencing, a portion of the reagents used in the synthesis of the complementary stretch of nucleic acids are dideoxynucleic acids which terminate the extension of a nucleic acid sequence. Four reactions are normally run each containing one of the four possible dideoxynucleic acids. As the dideoxynucleic acid in a given reaction is present at a low concentration relative to its comparable deoxynucleic acid it is not used at every occurrence in the sequence. The result is a series of extension products of various lengths depending upon the location at which the dideoxynucleic acid was incorporated. By also incorporating a detection system of some type, typically radioactive or fluorescent, it is possible to determine the sequence of nucleic acids in the region in question.

EXEMPLIFICATION

Example 1

Genomic DNA was isolated from peripheral blood mononuclear cells by the high salt extraction method of Miller et al. (*A simple salting out procedure for extracting DNA from human nucleated cells*. Nucleic Acids Res, 1988. 16(3): p. 1215) and resuspended in sterile water to a concentration of 1 $\mu g/\mu l$.

The PCR primer HD17-F3 (5'-GGC GCA CCT GGA AAA GC-3') (purchased from Operon Technologies, Inc. of Alameda, Calif.) was 5' end labeled with fluorescein by the incorporation of a fluorescein amidite during HD17-F3 synthesis by Operon Technologies.

Amplification of HD specific sequence was completed using primers HD17-F3 and HD17-R1 (5'-GCG GCT GAG GAA GCT GA-3') (Operon Technologies) obtained as HPLC purified stocks. Each PCR reaction contained the following: 100–500ng of genomic DNA, PCR buffer (10 mM Tris, pH 8.4, 50 mM KCl, 2 mM $MgCl_2$) (obtained from Sigma Chemical of St. Louis, MO), dNTP's (Pharmacia) to a final concentration of 200 $\mu M$ (50% of the dGTP content was 7-deaza-GTP (Pharmacia), 12.5 $\mu M$ HD17-R1, 3.1 pM HD17-F3, 9.4 pM fluorescein labelled HD17-F3, 2.5M BETAINE™ Mono hydrate (N,N,N, trimethylglycine, Sigma Chemical), sterile water. Reaction tubes were heated to 95° C. for three minutes prior to the addition of 5 units of Taq polymerase (obtained from AmpliTaq, Perkin-Elmer of Foster City, Calif.). The reactions were cycled in a Perkin-Elmer 480 thermal cycler at 95° C., 1 min., 62° C., 1 min., 74° C., 1 min. for a total of 30 cycles. Amplification products were analyzed using a 6% sequencing gel containing 8M urea on a Pharmacia A.L.F. automated sequencer. Sizing of bands was accomplished by comparison to a M13 sequence ladder run on each gel. Areas under the peaks were determined by using the Fragment Manager software package from Pharmacia.

Comparisons were made to identical DNA samples amplified with the identical primers in a PCR reaction mix described in Andrew, et al. (*The relationship between trinucleotide (CAG) repeat length and clinical features of Huntington's disease*. Nat Genet, 1993. 4(4): p. 398–403).

Table 1 demonstrates the effect BETAINE™ has on amplification of HD alleles. The maximum peak was selected for each lane by analysis of the area under each peak using the Fragment Manager software package which selects peaks based on height above a uniform baseline. The baseline for each curve was determined by drawing a line from the nadir of one peak to the next nadir region to normalize comparison between curves. The addition of N,N,N trimethylglycine increases the area under the selected peak, as compared to identical samples amplified without N,N,N trimethylglycine, by an average of 9 fold when analyzing a normal size HD allele and by an average of 19.5 fold when analyzing HD alleles in the affected range.

| | Normal Allele Area under peak | | Affected Allele Area under peak | | Fold increase with BETAINE | |
|---|---|---|---|---|---|---|
| Sample | BETAINE | No Betaine | BETAINE | No Betaine | Normal | Affected |
| 1 | 732.2 | 45.6 | 218.2 | 17.4 | 16.5 | 13 |
| 2 | 2207 | 188.4 | 890.3 | 33 | 1.2 | 27.5 |
| 3* | 1519.3/ 1212.7 | 413.1/ 286.8 | | | 4/4.5* | |
| 4 | 2654.2 | 322 | 264.2 | 15 | 8.5 | 18 |

*Sample taken from an individual with two normal alleles. Values indicated the area under the peak for each normal allele and the fold increase with BETAINE ™

Equivalents

Those skilled in the art will recognize, or be able to ascertain, using no more than routine experimentation many equivalents to the specific embodiments of the invention described herein. Such equivalents are intended to be encompassed by the following claims:

The invention claimed is:

1. In the procedure for sequencing a target nucleotide sequence containing trinucleotide repeats, the improvement comprising adding an effective amount of a trimethylglycine to the reaction mixture of a sequencing procedure wherein fewer sequencing products which do not correspond to the target nucleotide sequence are produced than would be produced in the absence of trimethylglycine.

2. The procedure of claim 1 wherein the target nucleotide sequence is DNA.

3. The procedure of claim 1 wherein the sequencing procedure is enzymatic sequencing.

* * * * *